US010792051B2

(12) United States Patent
Kohler et al.

(10) Patent No.: US 10,792,051 B2
(45) Date of Patent: Oct. 6, 2020

(54) DEBRIS REMOVING DRILLING SYSTEM WITH IRRIGATION

(71) Applicant: Conmed Corporation, Utica, NY (US)

(72) Inventors: Adam J. Kohler, Iowa City, IA (US); Andrew Kam, Odessa, FL (US); Philip Lahey, Largo, FL (US); James Hutter, Largo, FL (US); Joseph A. Fritz, Largo, FL (US)

(73) Assignee: Conmed Corporation, Utica, NY (US)

( * ) Notice: Subject to any disclaimer, the term of this patent is extended or adjusted under 35 U.S.C. 154(b) by 202 days.

(21) Appl. No.: 16/008,224

(22) Filed: Jun. 14, 2018

(65) Prior Publication Data

US 2018/0360475 A1   Dec. 20, 2018

Related U.S. Application Data

(60) Provisional application No. 62/519,383, filed on Jun. 14, 2017, provisional application No. 62/563,886, filed on Sep. 27, 2017.

(51) Int. Cl.
*A61B 17/16* (2006.01)
*A61B 17/17* (2006.01)

(52) U.S. Cl.
CPC .......... *A61B 17/1633* (2013.01); *A61B 17/17* (2013.01); *A61B 2217/005* (2013.01); *A61B 2217/007* (2013.01)

(58) Field of Classification Search
CPC ................ A61B 17/1633; A61B 17/17; A61B 2217/005; A61B 2217/007
See application file for complete search history.

(56) References Cited

U.S. PATENT DOCUMENTS

2007/0055282 A1* 3/2007 Muschler ........... A61B 10/0233 606/92

* cited by examiner

*Primary Examiner* — Christian A Sevilla
(74) *Attorney, Agent, or Firm* — Bond, Schoeneck & King, PLLC; Frederick J. M. Price

(57) ABSTRACT

An orthopedic drilling system having a collection chamber positioned between a drill guide and a drill bit proximately to the flute of the drill bit to evacuate debris and swarf from a drilling site. The drill bit may be cannulated to define a throughbore in communication with an irrigation inlet. The drill guide can reciprocate into and out of a hub and be connection to a suction source. The flute of the drill bit may have a first outer diameter that is larger than a second outer diameter of an intermediate portion of the drill bit positioned proximately to the flute to define the chamber between the drill bit and the drill guide. Alternatively, the drill guide may have a first inner diameter positioned about the flute of the drill bit and a second, larger inner diameter proximate to the flute to define the collection chamber.

15 Claims, 7 Drawing Sheets

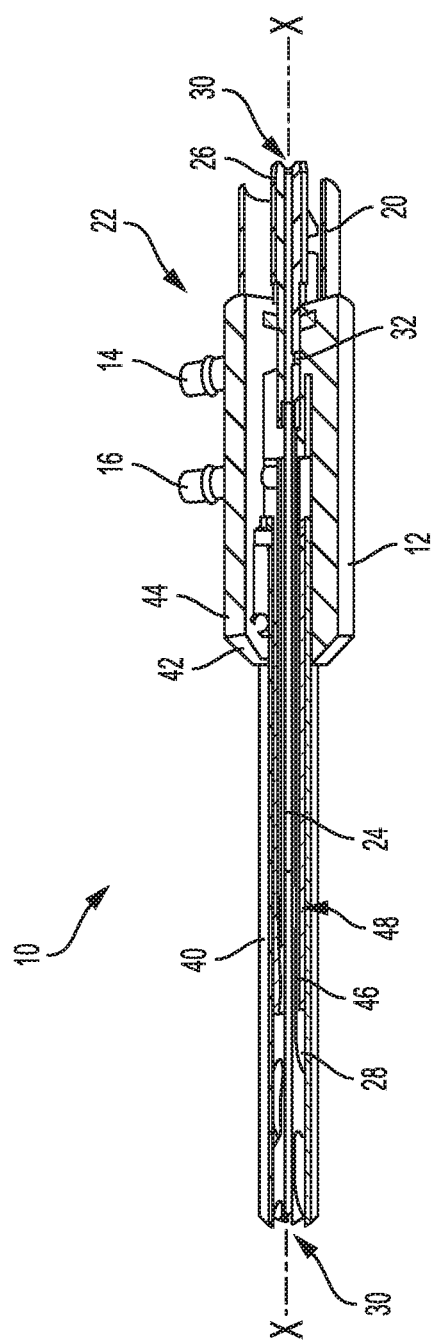
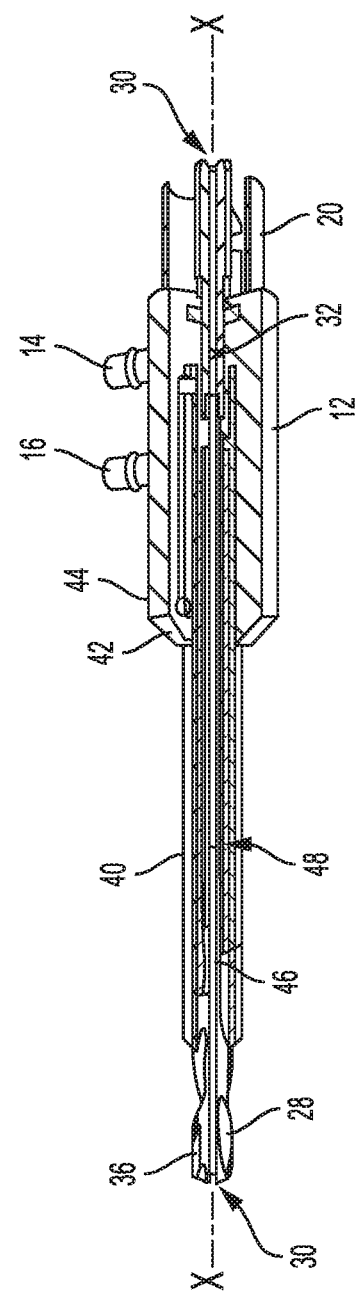
FIG. 1
FIG. 2

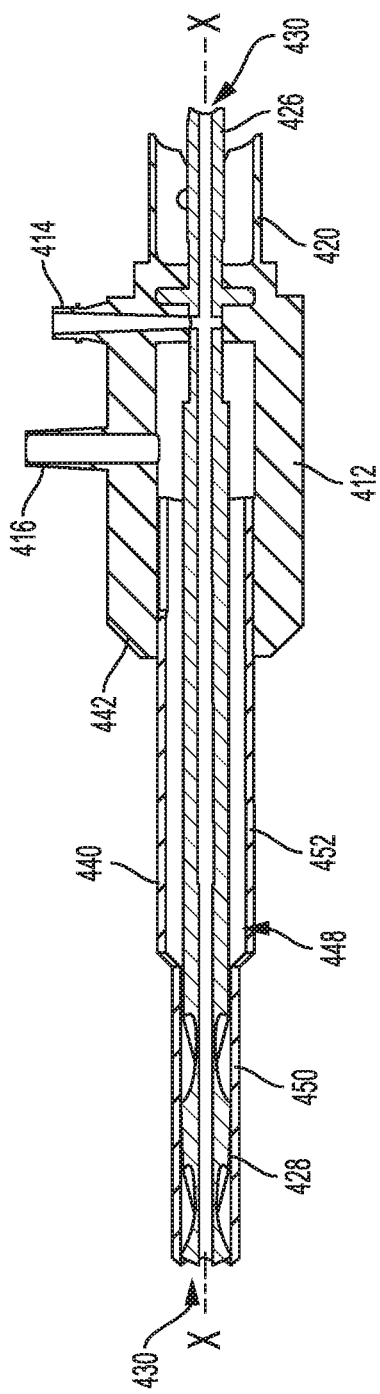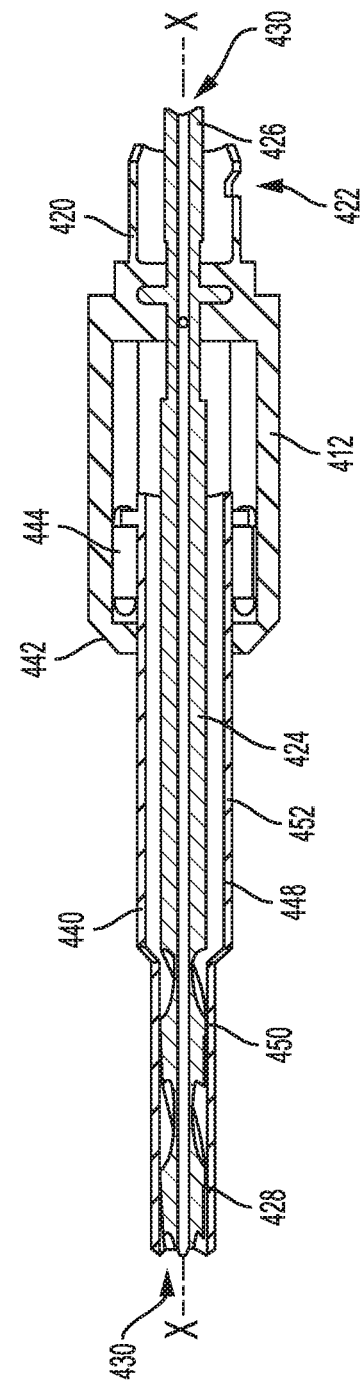

DEBRIS REMOVING DRILLING SYSTEM WITH IRRIGATION

CROSS-REFERENCE TO RELATED APPLICATIONS

The present application claims priority to U.S. Provisional App. No. 62/519,383, filed on Jun. 14, 2017 and U.S. Provisional App. No. 62/563,886, filed on Sep. 27, 2017.

BACKGROUND OF THE INVENTION

1. Field of the Invention

The present invention relates to orthopedic devices and, more particularly, to a drilling system that evacuates drilling debris during a procedure.

2. Description of the Related Art

Conventional orthopedic drills have an elongated shank that transitions into a fluted portion. During operation, material removed from a site (commonly referred to as swarf) will accumulate around the drill bit and the site. Swarf can obscure the drilling site, interfere with drilling, and results in overheating. As a result, conventional approaches to surgery involve the use of irrigation and suction to help clean debris from the site. In addition to only being moderately effective at removing swarf, the problems are exacerbated in medical revision surgeries where the drilling site includes bone as well as legacy medical implants manufactured from metals and plastics. For example, devices manufactured from polyether ether ketone (PEEK) present a particular problem due to the flexible nature of PEEK, which results in long strings of material being shed from a drilling site. These strings are particularly problematic as they tend to bind up around the drill bit. Accordingly, there is a need in the art for an orthopedic drill system that can more effectively address the accumulation of swarf in all orthopedic surgeries regardless of whether there are previously implanted medical devices at the site.

BRIEF SUMMARY OF THE INVENTION

The present invention is an orthopedic drilling system having a collection chamber positioned between a drill guide and a drill bit proximately to the flute of the drill bit to evacuate debris and swarf from a drilling site. The drill bit extends along a longitudinal axis from a shank to a flute. A drill guide extends from an end of the hub and encircles the drill bit. The drill guide and drill bit define a chamber extending circumferentially therebetween and positioned proximately to the flute. The drill guide may include a proximal end with a flange. The drill guide may include a distal end having conical face defining a ram. The system may further comprise a hub through which the drill bit extends. The hub may include irrigation inlet and a suction outlet. The suction outlet may be in communication with the chamber. The drill bit may be cannulated to define a throughbore and the throughbore may be in communication with the irrigation inlet. The drill guide can reciprocate into and out of the hub. The hub may include a spring interconnected to the drill guide to bias the drill guide along the longitudinal axis. The flute may have a first outer diameter and the drill bit has an intermediate portion positioned proximately to the flute and having a second outer diameter that is smaller than the first outer diameter to define the chamber between the drill bit and the drill guide. The drill guide may include a conical face defining a ram. The drill bit may include an irrigation port that provides communication between the irrigation inlet and the throughbore of the drill bit when the drill is rotated about the longitudinal axis. The drill guide may have distal portion with a first inner diameter positioned proximately to the flute and an intermediate portion positioned proximately to the distal portion and having a second inner diameter that is larger than the first inner diameter to define the chamber between the drill bit and the drill guide. The drill guide may have a conical face defining a ram. The drill bit may include an irrigation port that provides communication between the irrigation inlet and the throughbore of the drill bit when the drill is rotated about the longitudinal axis.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 1 is a cross-section of an embodiment of an orthopedic drill system according to the present invention;

FIG. 2 is another cross-section of an embodiment of an orthopedic drill system according to the present invention;

FIG. 15 is a cross-section of the embodiment of FIG. 12; and

FIG. 16 is another cross-section of the embodiment of FIG. 12.

DETAILED DESCRIPTION OF THE INVENTION

Figure 3:
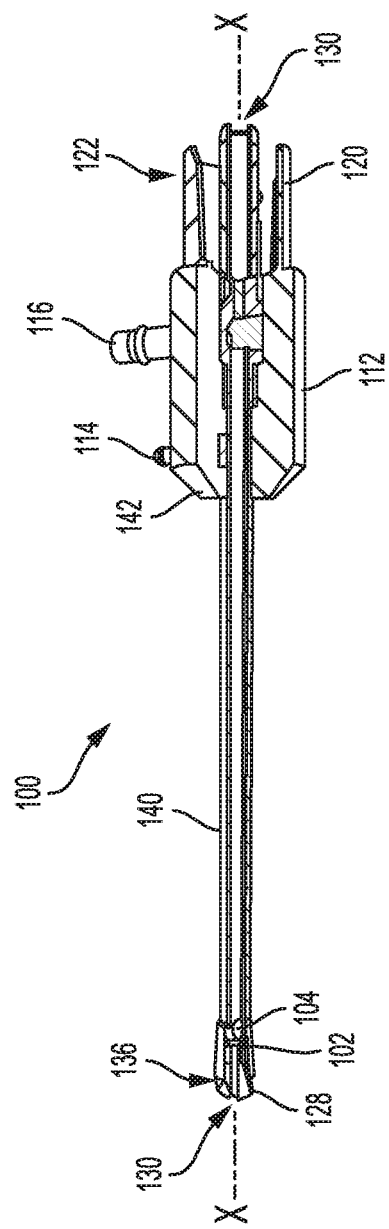
FIG. 3 is a cross-section of another embodiment of an orthopedic drill system according to the present invention.
Figure 4:
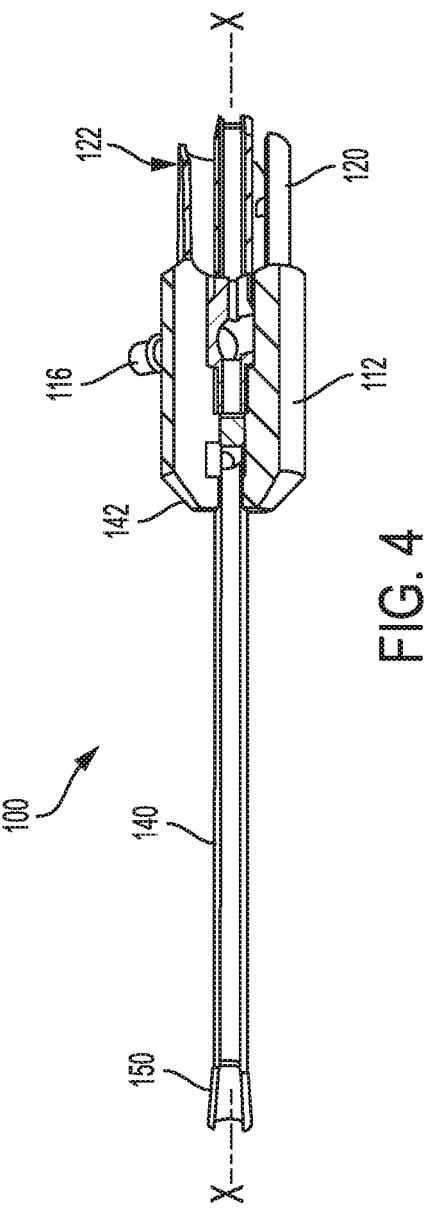
FIG. 4 is another cross-section of the embodiment of FIG. 3.
Figure 5:
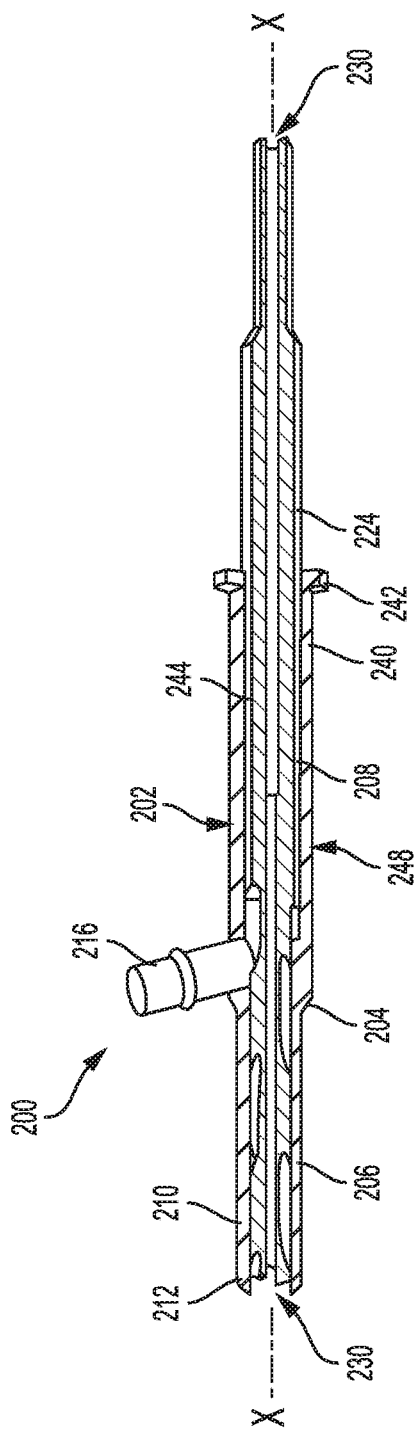
FIG. 5 is a cross-section of a further embodiment of an orthopedic drill system according to the present invention.
Figure 6:
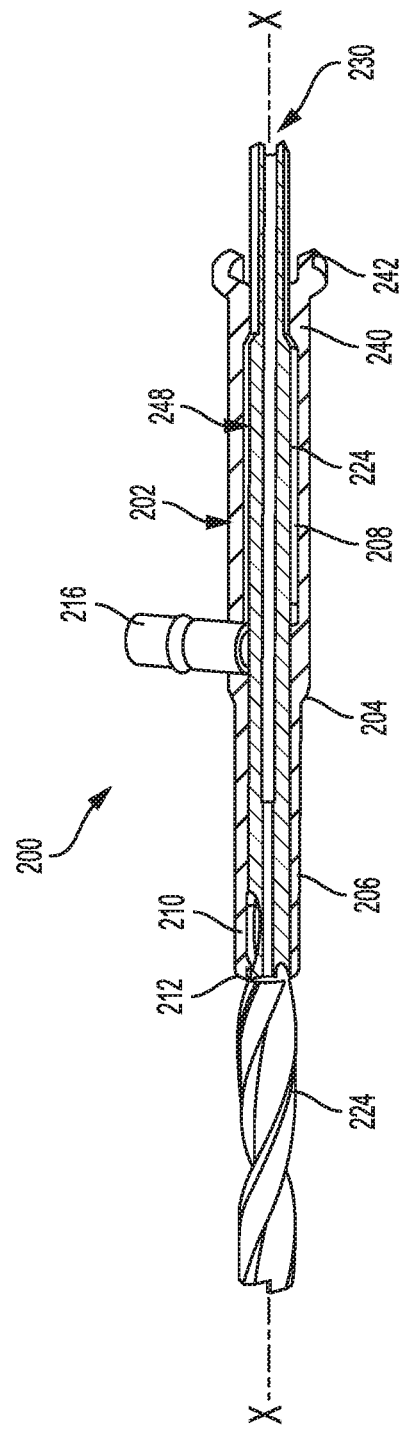
FIG. 6 is another cross-section of the embodiment of FIG. 5.
Figure 7:
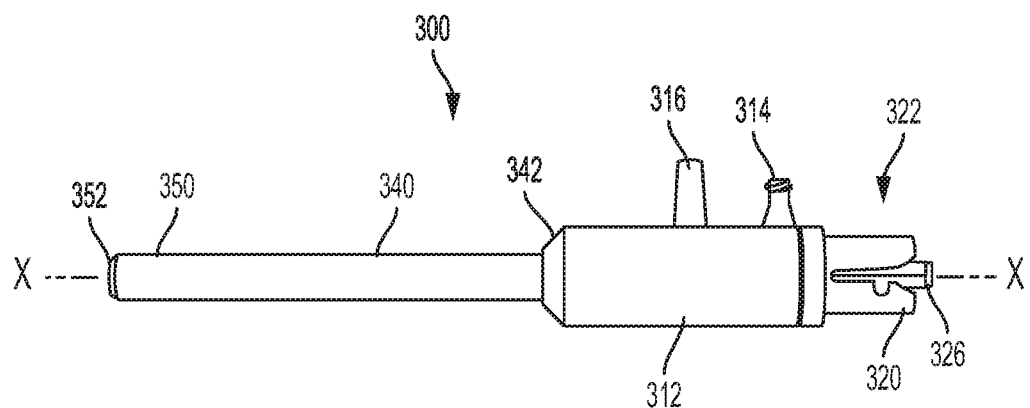
FIG. 7 is a perspective view of an additional embodiment of an orthopedic drill system according to the present invention.
Figure 8:
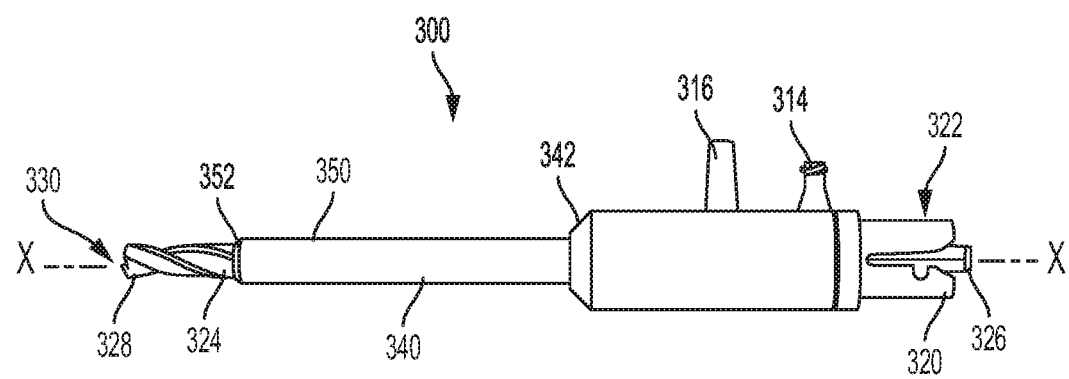
FIG. 8 is another perspective view of the embodiment of FIG. 7.
Figure 9:
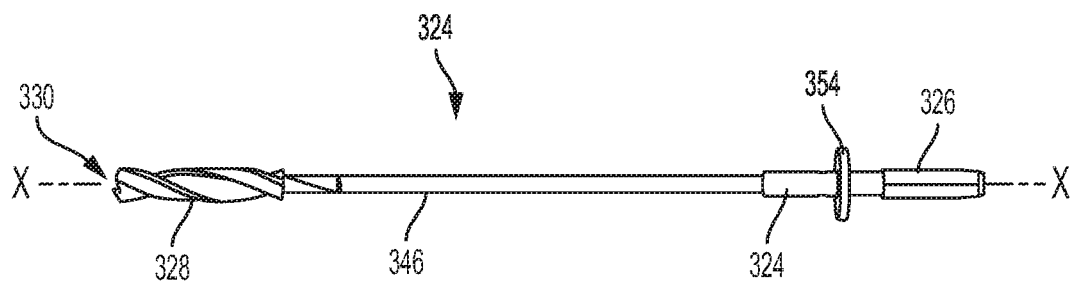
FIG. 9 is a perspective view of the drill bit of the embodiment of FIG. 7.
Figure 10:
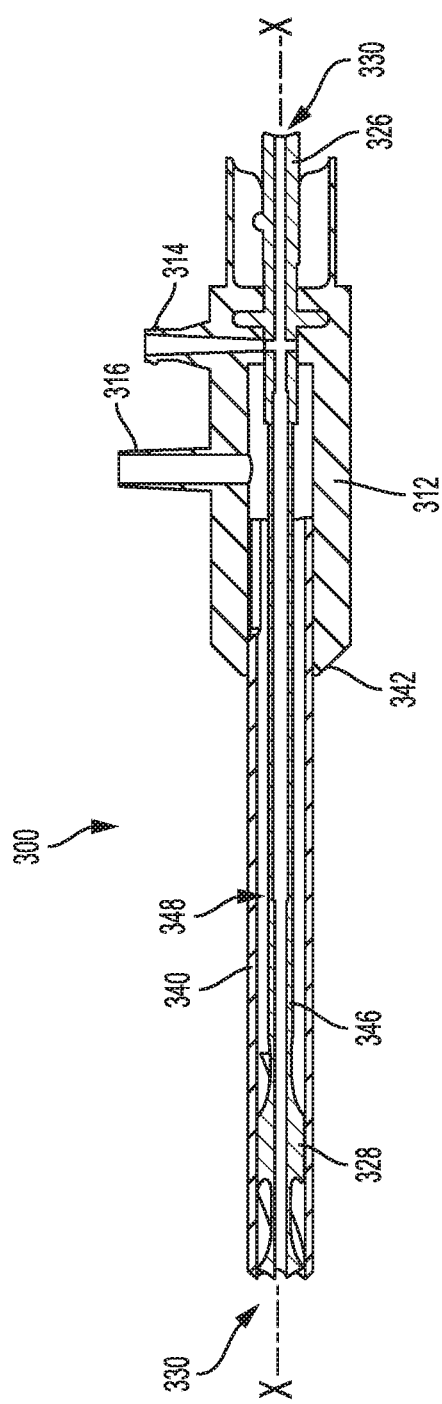
FIG. 10 is a cross-section of the embodiment of FIG. 7.
Figure 11:
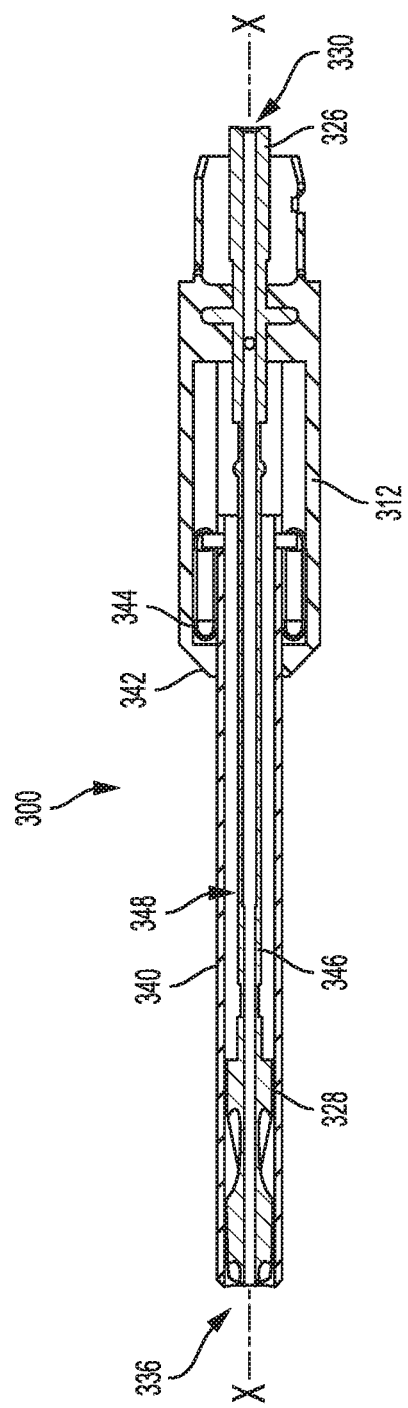
FIG. 11 is another cross-section of the embodiment of FIG. 7.
Figure 12:
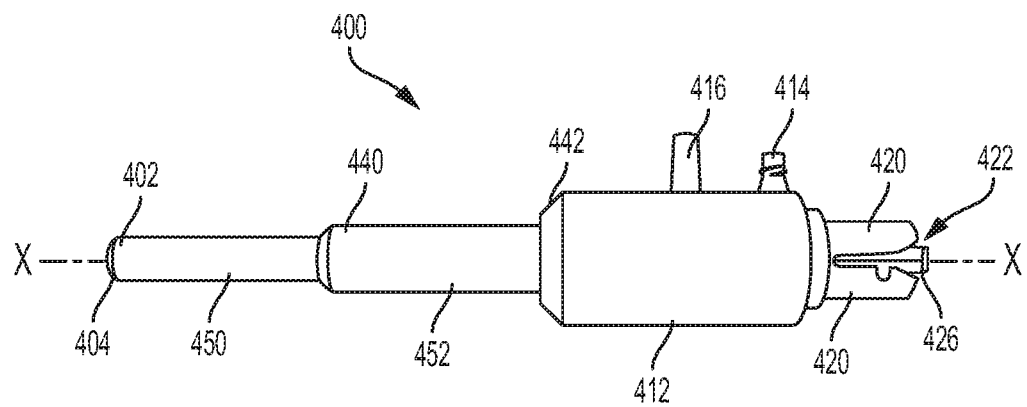
FIG. 12 is a perspective view of yet another embodiment of an orthopedic drill system according to the present invention.
Figure 13:
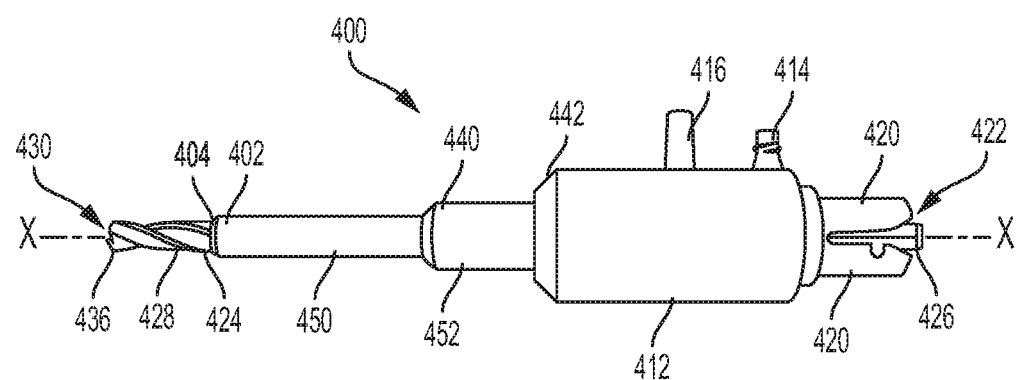
FIG. 13 is another perspective view of the embodiment of FIG. 12.
Figure 14:
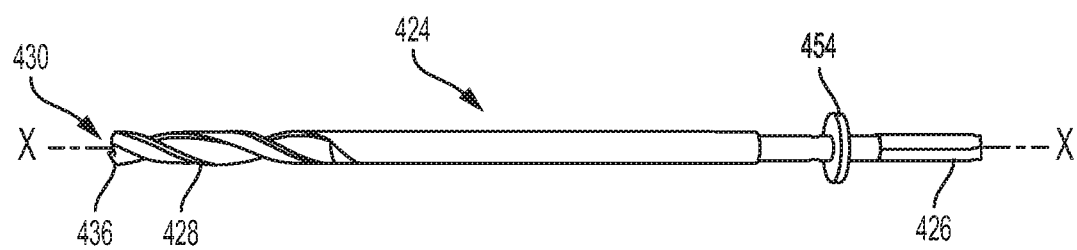
FIG. 14 is a perspective view of the drill bit of the embodiment of FIG. 12.

Referring to the figures, wherein like numeral refer to like parts throughout, there is seen in FIG. 1 an orthopedic drill system 10 comprising a hub 12 including an inlet 14 for interconnection to an irrigation source and an outlet 16 for interconnection to a vacuum source. Hub 12 includes tabs 20 positioned at a proximal end 22 for coupling to an orthopedic hand piece. A drill bit 24 extending longitudinally along axis X-X through hub 12 from a shank 26 to a flute 28.

Shank 26 is configured for connection to an orthopedic drill and thus may have a hexagonal shape for mating with standard drills. It should be recognized that other non-circular geometries may be used for coupling shank 26 to a particular model drill. Drill bit 24 may be cannulated to include a throughbore 30 extending along axis X-X for, among other things, accepting a guide wire as is typical for use in precisely positioning orthopedic drills. Drill bit 24 includes an irrigation port 32 in communication with inlet 14 of hub 12 so that irrigation fluid may be provided into throughbore 30 of drill bit 24. Irrigation fluid is free to pass through throughbore 30 and exit drill bit 24 at its distal end 36.

System 10 further comprises a drill guide 40 extending from the distal end 42 of hub 12. Drill guide 40 is biased by a spring 44 positioned in hub 12 so that drill guide 40 may reciprocate partially into and back out of hub 12 during operation. Drill bit 24 includes an intermediate portion 46 positioned proximately to flute 28 and having a smaller outer diameter than flute 28. Intermediation portion 46 and drill guide 40 define a chamber 48 extending circumferentially about axis X-X and between intermediate portion 46 and drill guide 40. Chamber 48 extends into hub 12 and is in fluid communication with outlet 16 so that suction provided to outlet 16 will draw any irrigation fluid, debris, or swarf into the distal end of intermediate portion 46 and then through chamber 48 to outlet 16. In operation, swarf produced at a site, including any plastic debris from a legacy implant, will be drawn along flute 28 into chamber 48 to collect about intermediate portion 46 and thus away from the drilling site. The removal of the swarf from the site in this manner reduces the amount of debris and amount of heat produced at the site. Chamber 48 may include a door or a cover that allows for communication from the exterior of system 10 so that debris can be cleared from chamber 48 for additional drilling operations.

In another embodiment, system 100 has a hub 112 including an inlet 114 for interconnection to an irrigation source and an outlet 116 for interconnection to a vacuum source. Hub 112 includes tabs 120 positioned at a proximal end 122 for coupling to a hand piece. A drill bit 124 extends longitudinally along axis X-X through hub 112 from a shank 126 to a flute 128. Drill bit 124 may be cannulated to include a throughbore 130 extending along axis X-X for, among other things, accepting a guide wire as is typical for use in precisely positioning orthopedic drills. The distal end of flute 128 includes a taper 102 that feeds into a cut 104 in communication with throughbore 130 of drill bit 124. System 10 further comprises an outer tube 140 fixed to and extending from the distal end 142 of hub 112. Outer tube 140 is spaced apart from and extends around drill bit 124 to define an irrigation chamber 148 extending along axis X-X. Outer tube 140 is in communication with inlet 114 to direct irrigation fluid around drill bit 124 to distal end 136 of drill bit 124. The distal tip 150 of outer tube 140 is flared outwardly and spaced apart from taper 102 to funnel debris inwardly toward cut 104 for removal via suction through throughbore 130. Distal end 136 of drill bit 124 is preferably an acorn style so that its outer diameter corresponds to the outer diameter of outer tube 140, thereby allowing outer tube 140 to be inserted along with drill bit 124 into a bone tunnel as it is being formed with minimal contact against the interior surface of the bone tunnel. Chamber 148 may include a door or a cover that allows for communication from the exterior of system 10 so that debris can be cleared from chamber 148 for additional drilling operations.

In another embodiment, system 200 comprises a drill guide 202 having an outlet 216 for connection to a vacuum source. A drill bit 224 extends longitudinally through drill guide 202 and is cannulated to include a throughbore 230. Drill guide 202 is coupled to drill bit 224 by a spring 244 that allows drill bit 224 to reciprocate partially into and out of drill guide 202. Drill guide 202 includes a step 204 along an intermediate portion to define a distal portion 206 having an inner diameter corresponding closely to the outer diameter of drill bit 224 and a proximal portion 208 with a larger inner diameter to define a collection chamber 248 extending circumferentially about drill bit 224 for receiving debris and swarf during drilling. Debris collection chamber 248 is in communication with outlet 216. Drill guide 202 includes a distal end 210 with a ram 214 having a sharp conical face for bone engagement. A proximal end 240 of drill guide 224 has a flange 242 that allows for tapping of drill guide 202 with a mallet. Chamber 248 may include a door or a cover that allows for communication from the exterior of system 10 so that debris can be cleared from chamber 248 for additional drilling operations.

In another embodiment, system 300 has a hub 312 including an inlet 314 configured with a luer lock for interconnection to an irrigation source and an outlet 316 for interconnection to a vacuum source. Hub 312 includes tabs 320 positioned at a proximal end 322 for coupling to a hand piece in lieu of a chuck. A drill bit 324 extends longitudinally along axis X-X through hub 312 from a hexagonal shank 326 to a flute 328. Drill bit 324 is cannulated to include a throughbore 330 extending along axis X-X for, among other things, accepting a guide wire as is typical for use in precisely positioning orthopedic drills. Drill bit 324 includes an intermediate portion 346 having a smaller diameter positioned proximately to flute 328 and extending into hub 312. A drill guide 340 extends from the distal end 342 of hub 312 and is biased by a spring 344 positioned in hub 312 so that drill guide 340 may reciprocate partially into and back out of hub 312. Intermediation portion 346 of drill bit 324 cooperates with drill guide 340 to define a collection chamber 348 extending circumferentially about drill bit 324 for receiving debris and swarf during drilling. Collection chamber 348 is in communication with outlet 316 for removal of loose debris along with any irrigation fluid. Collection chamber 348 is dimensioned to collect plastic material, such as PEEK, that may be removed from a site during drilling operations where a legacy device is present. Distal end 350 of drill guide 340 may include a conical ram 352 to allow for bone engagement and to provide a tight seal against the interior surface of a bone tunnel as it is being formed so that all debris is collected by system 300. Drill bit 324 may include a stop 354 to restrict reciprocation of drill bit 324 into and out of hub 312. Chamber 348 may include a door or a cover that allows for communication from the exterior of system 10 so that debris can be cleared from chamber 348 for additional drilling operations.

In another embodiment, system 400 has a hub 412 including an inlet 414 configured with a luer lock for interconnection to an irrigation source and an outlet 416 for interconnection to a vacuum source. Hub 412 includes tabs 420 positioned at a proximal end 422 for coupling to a hand piece in lieu of a chuck. A drill bit 424 extends longitudinally along axis X-X through hub 412 from a hexagonal shank 426 to a flute 428. Drill bit 424 is cannulated to include a throughbore 430 extending along axis X-X for, among other things, accepting a guide wire as is typical for use in precisely positioning orthopedic drills. Drill bit 424 includes an irrigation port 432 in communication with inlet 414 so that irrigation supplied to inlet 414 will pass through throughbore 430 and out of the distal end 436 of drill bit 424. A drill guide 440 extends from the distal end 442 of hub 412 and is biased by a spring 444 positioned in hub 412 so that drill guide 440 may reciprocate partially into and out of hub 412. Drill guide 440 has a distal portion 450 with a first inner diameter that closely surrounds flute 428 of drill bit 424. Drill guide 440 includes an intermediate portion 452 located proximately to distal portion 450 and having a larger inner diameter to define a collection chamber 448 extending circumferentially about drill bit 424 that extends through chamber 448. Collection chamber 448 is in communication with outlet 416 for removal of loose debris along with any irrigation fluid. Collection chamber 448 is dimensioned to collect plastic material, such as PEEK, that may be removed from a site during drilling operations where a legacy device is present. Distal end 402 of drill guide 440 may include a conical ram 404 to allow for bone engagement and to provide a tight seal against the interior surface of a bone tunnel as it is being formed so that all debris is collected by system 400. Drill bit 424 may include a stop 454 to restrict reciprocation of drill bit 424 into and out of hub 412. Chamber 448 may include a door or a cover that allows for communication from the exterior of system 10 so that debris can be cleared from chamber 448 for additional drilling operations.

As described herein, the various embodiments of the invention allow for the collection of debris and swarf from an orthopedic drilling site, thereby reducing debris interference and avoiding an increase in temperature. The invention is particularly useful with respect to revision surgeries where a legacy medical device may be in place and involved in drilling operations as the invention allows for removal of plastic and metal swarf from the drilling site.

What is claimed is:

1. An orthopedic drilling system, comprising:
   a drill bit extending along a longitudinal axis from a shank to a flute;
   a drill guide extending along and encircling the drill bit, wherein the drill guide includes a distal end having conical face defining a ram;
   wherein a portion of the drill guide and a portion of drill bit are separated from each other to define a debris collection chamber that extends circumferentially therebetween and is positioned proximately to the flute of the drill bit to collect any debris created by flute.
2. The system of claim 1, wherein the drill guide includes a proximal end with a flange.
3. The system of claim 1, further comprising a hub through which the drill bit extends.
4. The system of claim 3, wherein the hub includes an irrigation inlet and a suction outlet.
5. The system of claim 4, wherein the suction outlet is in communication with the chamber.
6. The system of claim 5, wherein the drill bit is cannulated to define a throughbore and the throughbore is in communication with the irrigation inlet.
7. The system of claim 6, wherein the drill guide can reciprocate into and out of the hub.
8. The system of claim 6, wherein the hub includes a spring interconnected to the drill guide to bias the drill guide along the longitudinal axis.
9. The system of claim 1, wherein the flute has a first outer diameter and an intermediate portion of the drill bit that is positioned proximately to the flute has a second outer diameter that is smaller than the first outer diameter to define the chamber between the drill bit and the drill guide.
10. The system of claim 1, wherein the drill bit includes an irrigation port that provides for communication between an irrigation inlet and a throughbore of the drill bit.
11. The system of claim 1, wherein the drill guide has distal portion with a first inner diameter positioned proximately to the flute and an intermediate portion positioned proximately to the distal portion and having a second inner diameter that is larger than the first inner diameter to define the debris collection chamber between the drill bit and the drill guide.
12. An orthopedic drilling system, comprising:
    a drill bit extending along a longitudinal axis from a shank to a flute;
    a drill guide extending along and encircling the drill bit;
    wherein a portion of the drill guide and a portion of drill bit are separated from each other to define a debris collection chamber that extends circumferentially therebetween and is positioned proximately to the flute of the drill bit to collect any debris created by flute; and
    a hub through which the drill bit extends wherein the drill guide can reciprocate into and out of the hub.
13. An orthopedic drilling system, comprising:
    a drill bit extending along a longitudinal axis from a shank to a flute;
    a drill guide extending along and encircling the drill bit;
    wherein a portion of the drill guide and a portion of drill bit are separated from each other to define a debris collection chamber that extends circumferentially therebetween and is positioned proximately to the flute of the drill bit to collect any debris created by flute; and
    a hub through which the drill bit extends wherein the hub includes a spring interconnected to the drill guide to bias the drill guide along the longitudinal axis.
14. An orthopedic drilling system, comprising:
    a drill bit extending along a longitudinal axis from a shank to a flute, wherein the drill bit includes an irrigation port that provides for communication between an irrigation inlet and a throughbore of the drill bit;
    a drill guide extending along and encircling the drill bit;
    wherein a portion of the drill guide and a portion of drill bit are separated from each other to define a debris collection chamber that extends circumferentially therebetween and is positioned proximately to the flute of the drill bit to collect any debris created by flute.
15. An orthopedic drilling system, comprising:
    a drill bit extending along a longitudinal axis from a shank to a flute;
    a drill guide extending along and encircling the drill bit, wherein the drill guide has distal portion with a first inner diameter positioned proximately to the flute and an intermediate portion positioned proximately to the distal portion and having a second inner diameter that is larger than the first inner diameter to define the debris collection chamber between the drill bit and the drill guide;
    wherein a portion of the drill guide and a portion of drill bit are separated from each other to define a debris collection chamber that extends circumferentially therebetween and is positioned proximately to the flute of the drill bit to collect any debris created by flute.

* * * * *

UNITED STATES PATENT AND TRADEMARK OFFICE
CERTIFICATE OF CORRECTION

PATENT NO. : 10,792,051 B2
APPLICATION NO. : 16/008224
DATED : October 6, 2020
INVENTOR(S) : Adam J. Kohler et al.

It is certified that error appears in the above-identified patent and that said Letters Patent is hereby corrected as shown below:

In the Specification

Column 5, Line 42, please add "the" between "of" and "drill"
Column 5, Line 46, please add "the" between "by" and "flute"
Column 6, Line 7, please add "a" after "has"
Column 6, Line 18, please add "the" between "of" and "drill"
Column 6, Line 22, please add "the" between "by" and "flute"
Column 6, Line 29, please add "the" between "of" and "drill"
Column 6, Line 33, please add "the" between "by" and "flute"
Column 6, Line 43, please add "the" between "of" and "drill"
Column 6, Line 47, please add "the" between "by" and "flute"
Column 6, Line 52, please add "a" between "has" and "distal"
Column 6, Line 59, please add "the" between "of" and "drill"
Column 6, Line 63, please add "the" between "by" and "flute"

Signed and Sealed this
Third Day of May, 2022

Katherine Kelly Vidal
*Director of the United States Patent and Trademark Office*